United States Patent [19]

Ahlers

[11] Patent Number: 5,016,702

[45] Date of Patent: May 21, 1991

[54] METHOD OF PRODUCING OPEN-CELLED METAL STRUCTURES

[75] Inventor: Olaf Ahlers, Hamburg, Fed. Rep. of Germany

[73] Assignee: Eska Medical Lubeck Medizintechnik GmbH & Co., Lubeck, Fed. Rep. of Germany

[21] Appl. No.: 572,725

[22] Filed: Aug. 24, 1990

[30] Foreign Application Priority Data

Aug. 28, 1989 [DE] Fed. Rep. of Germany ....... 3928394

[51] Int. Cl.$^5$ ............................ B22C 3/00; B22C 7/02; B22D 23/00; B22D 25/00
[52] U.S. Cl. ........................................ 164/34; 164/35; 164/45; 264/221
[58] Field of Search ..................... 164/34, 35, 36, 45, 164/79; 264/59, 221, DIG. 44

[56] References Cited

U.S. PATENT DOCUMENTS

| | | | |
|---|---|---|---|
| 3,616,841 | 11/1971 | Walz | 164/34 |
| 3,845,181 | 10/1974 | Ravault | 264/59 X |
| 3,899,556 | 8/1975 | Heide et al. | 264/DIG. 44 X |
| 3,946,039 | 3/1976 | Walz | 164/34 X |
| 4,600,546 | 7/1986 | Grundei | 164/34 X |
| 4,781,721 | 11/1988 | Grundei | 623/16 |
| 4,812,278 | 3/1989 | Natori et al. | 164/36 X |

FOREIGN PATENT DOCUMENTS

| | | | |
|---|---|---|---|
| 3106917 | 11/1982 | Fed. Rep. of Germany. | |
| 3224265 | 1/1984 | Fed. Rep. of Germany. | |
| 1308958 | 3/1973 | United Kingdom | 264/221 |

Primary Examiner—J. Reed Batten, Jr.
Attorney, Agent, or Firm—Panitch Schwarze Jacobs & Nadel

[57] ABSTRACT

Open-celled metal structures are produced which have walls and webs of uniform strength throughout. The structures may also have an irregular surface pattern. To make a strengthened positive pattern, the method comprises application of at least one layer of a strengthening agent such as poly(methyl methacrylate) or polyester resin to a plastic substrate used for ceramic mold formation. The strengthened positive pattern is embedded in a ceramic mass, and heated to incinerate and remove the plastic substrate, which results in voids in the ceramic mass. Molten metal is poured into the ceramic mass. After solidification, the ceramic mass is removed to form the open-celled metal structure.

13 Claims, No Drawings

METHOD OF PRODUCING OPEN-CELLED METAL STRUCTURES

BACKGROUND OF THE INVENTION

This invention relates to a method of producing a metal structure having an open cell structure at least partly covering its surface, useful as a component of bone implants. Upon implantation, bone material grows into the open-celled structure produced by the method of the invention thereby assuring permanent fixation of the implant in the bone. Another aspect of this invention pertains to a method of producing metal open-celled structures wherein the surface structure is very irregular. When implanted, the irregular surface structure stimulates bone growth.

Open-celled metal structures are produced using a lost positive pattern. In general, the voids of a suitable positive pattern are filled with a ceramic encapsulating medium and the material of the positive pattern is volatilized or otherwise removed by heating thereby forming a ceramic mold. The voids of the mold are then filled with metal and after hardening of the metal, the ceramic mold is removed.

In one prior art method of making an open-celled structure disclosed in German Offenlegungsschrift 3106917 (U.S. Pat. No. 4,781,721), a sponge of natural or synthetic material was used as a positive pattern. This method of producing open-celled metal structures has proved unsatisfactory in that the walls and the interlinking webs of a sponge are so thin that the metal structure produced using the sponge positive lacks sufficient strength.

Another method for producing open-celled metal structures has been disclosed in German Offenlegungsschrift 3224265 (U.S. Pat. No. 4,600,546). In this disclosure, wax is used as a strengthening means for the walls and cross-linked webs of a porous shaped plastic substrate. Wax in liquid form or as an emulsion in water is deposited on the plastic substrate and, after drying, is protected with a coating of plastic enamel. Within certain limits, the method disclosed produces thicker walls and interlinking webs in the plastic substrate than those of the prior art method discussed above.

However, this prior art method has a disadvantage in that the wax, which was applied by dipping or spraying onto the plastic substrate and as coated by the enamel, is inelastic compared to the elastic shaped plastic substrate. Therefore, under pressure, the wax can easily separate from the walls and webs of the pores of the plastic substrate. Another disadvantage is that the walls and webs of the plastic substrate take on a negative charge with respect to the wax or wax-in-water emulsion. Consequently, there is no uniform bond between the walls and webs of the plastic substrate and the wax, especially within the deep recesses of the plastic substrate. The rheological characteristics of the wax or wax-in-water emulsion do not allow the walls and webs deep within the plastic substrate to be strengthened to a satisfactory degree. As a result, the plastic substrate produced by this method has within it walls and webs which are in some cases too thin to withstand long-term stresses.

Accordingly, there exists a need for a method to produce open-celled metal structures wherein the walls, webs and pores of the plastic substrate are of a uniform and reliable strength throughout. Moreover, the means used to strengthen the walls and webs of the substrate must be capable of volatilization or destruction by heat, such as by incineration.

SUMMARY OF THE INVENTION

In accordance with the present invention, there is provided a method for producing open-celled metal structures. The method comprises cleaning an open-pored plastic substrate formed over a wax foundation, wherein the pores have an average width of about 1 to about 3 mm; applying at least one layer of a strengthening agent selected from the group consisting of poly(methyl methacrylate) and polyester resin in a solvent to the cleaned plastic substrate which, after hardening, produces a strengthened substrate; embedding the strengthened substrate as a whole in a ceramic mass; heating the ceramic mass to melt the wax foundation and incinerate the strengthened plastic substrate, leaving voids in the remaining ceramic mass; filling the voids in the ceramic mass with molten metal; allowing the metal to harden; and removing the ceramic material.

DETAILED DESCRIPTION OF THE PREFERRED EMBODIMENTS

In the method of the invention, a plastic substrate with a wax foundation having an average pore width preferably in a range of about 1 to about 3 mm is cleaned with a solvent such as acetone. The plastic substrate is then sprayed all over with at least one layer of a solution of poly(methyl methacrylate) (PMMA) or a solution of polyester resin in a solvent. The PMMA or the resin strengthens the walls and the cross-linked webs of the plastic substrate.

If PMMA is used as a strengthening agent, acetone is suitable as a solvent. However, if polyester resin is used a strengthening agent, then a nitrolacquer solvent can be used.

In both cases, the solvent partly dissolves the surface of the plastic substrate. Moreover, the solvent evaporates relatively quickly leaving the resin on the substrate as a strengthening layer. By partly dissolving the surface of the plastic substrate, a capillary effect is produced whereby the applied strengthening agents can penetrate to the deepest layers within the plastic substrate even if the spray does not directly reach such areas. The strengthening agent remaining on the walls and webs of the plastic substrate can easily be volatilized or incinerated upon heating. If a relatively thick strengthening layer of the walls and webs of the plastic substrate is required, several layers of the strengthening agent can be applied, preferably after each prior layer hardens. It is preferred that individual layers have different colors, thereby making it possible to check the consistency of the layer thicknesses under a microscope.

In a preferred embodiment of the method of the invention, after each previously applied layer of strengthening agent has hardened, the plastic substrate is moistened throughout with a keying resin film which partially dissolves the surface of the last layer of the strengthening agent. After application of the keying resin film, at least one layer of an auto-cross-linking two-part silicone is applied, preferably at a temperature of less than 12° C., to the plastic substrate. Preferably, the two-part silicone is an unsaturated two component silicone rubber that cross-links at ambient temperature. The cross-linking can be accelerated by quenching the plastic substrate in water after application of the two-part silicone. The use of the keying resin imparts an irregular surface structure to the plastic substrate. The irregular surface structure is desirable in that it stimulates bone growth into the open-celled metal structure more quickly.

The average width of the pores of the plastic substrate is preferably within the range of about 1 to about 3 mm. The metal structure produced according to the method of the present invention has larger pores and sharper edges on its outside surface than the prior art structures. Because of the size of the pores, it is possible for bone fibrils to grow deep into the pores. The sharp edges on the outside of the metal structure are due to the fact that when cutting the plastic substrate of the positive pattern to size, there is a considerably higher probablility of cutting through larger pores than when cutting a plastic substrate with smaller pores.

In a presently preferred embodiment, the keying resin film and the two-part silicone each comprise unsaturated silicone resin. In this embodiment, an attraction exists between the silicone resin and the two-part silicone, whereby the walls and webs of the pores of the plastic substrate are substantially strengthened in a uniform manner throughout the substrate. It is believed that a type of capillary action results in the strengthening agent and any additional two-part silicone rubber reaching into the deepest areas within the substrate.

In another presently preferred embodiment, additional strengthening of the irregular surface structure of the plastic substrate can be achieved by applying a two-part polyurethane resin preferably at a temperature of less than 12° C., after the two-part silicone layer has been applied. The two-part polyurethane resin binds tightly to the two-part silicone by its ability to partly dissolve the two-part silicone.

The PMMA or polyester resin solution preferably should be stored and applied at a temperature of less than 12° C., because the solvents for the PMMA or polyester resin, such as acetone or the nitrolacquer solvent, have a low vaporization temperature. At higher temperatures, for example at room temperature, the solvent vaporizes so quickly that the concentration ratios would change too quickly to carry out the spraying step of the method, particularly when mass-producing the implants. Preferably, a 25% v/v solution of PMMA or polyester resin in solvent is used. At this dilution, the solution can be easily sprayed by means of a spray gun. Accordingly, the concentration ratios of the strengthening agent and solvent do not change significantly during application, thus assuring uniform thickness of the strengthening agent when mass producing the substrates.

The present invention may be embodied in other specific forms without departing from the spirit or essential attributes thereof and, accordingly, reference should be made to the appended claims, rather than to the foregoing specification as indicating the scope of the invention.

I claim:

1. A method for producing an open-celled metal structure comprising the steps of:
   (a) cleaning an open-pored plastic substrate formed over a wave foundation, wherein the pores have an average width of about 1 to about 3 mm;
   (b) applying at least one layer of a strengthening agent selected from the group consisting of poly(methyl methacrylate) and polyester resin in a solvent to the cleaned plastic substrate, whereby the solvent partly dissolves the substrate surface, which layer, after hardening, produces a strengthened porous substrate;
   (c) embedding the strengthened substrate as a whole in a ceramic mass;
   (d) heating the ceramic mass to melt the wax foundation an dincinerate the strengthened plastic substrate, leaving voids in the remaining ceramic mass;
   (e) filling the voids in the ceramic mass with molten metal;
   (f) allowing the metal to harden; and
   (g) removing the ceramic material.

2. The method of claim 1 wherein step (b) is repeated several times, each repeated application occurring after the prior layer of strengthening agent has hardened.

3. The method of claim 1 further comprising an additional step after step (b) of
   (b) (i) strengthening the plastic substrate further by applying a keying resin which partially dissovles the last hardened layer of the strengthening agent of step (b) followed by
   (b) (ii) applying at least one layer of an auto-cross-linking two-part silicone.

4. The method of claim 3 further comprising
   (b) (iii) applying a layer of a two-part polyurethane resin after cross-linking of the two-part silicone layer.

5. The method of claim 3, wherein the keying resin comprises unsaturated silicone resin.

6. The method of claim 3, wherein the two-part silicone comprises unsaturated two-part silicone rubber which cross-links at ambient temperature.

7. The method of claim 1, wherein each strengthening layer has a different color.

8. The method of claim 2, wherein each strengthening layer has a different color.

9. The method of claim 3, wherein each strengthening layer has a different color.

10. The method of claim 4, wherein each strengthening layer has a different color.

11. The method of claim 1, wherein the strengthening agent is applied at a temperature of less than about 12° C.

12. The method of claim 3, wherein the two-part silicone is applied at a temperature of less than about 12° C.

13. The method of claim 4, wherein the two-part polyurethane resin is applied at a temperature of less than about 12° C.

* * * * *

UNITED STATES PATENT AND TRADEMARK OFFICE
CERTIFICATE OF CORRECTION

PATENT NO. : 5,016,702
DATED      : May 21, 1991
INVENTOR(S) : Olaf Ahlers

It is certified that error appears in the above-identified patent and that said Letters Patent is hereby corrected as shown below:

Column 4,

Claim 1, line 4, "wave" should read --wax--;

line 16, "an dincinerate" should read --and incinerate--.

Signed and Sealed this

Thirtieth Day of March, 1993

Attest:

STEPHEN G. KUNIN

Attesting Officer        Acting Commissioner of Patents and Trademarks